United States Patent [19]

Iioka et al.

[11] Patent Number: 4,469,673

[45] Date of Patent: Sep. 4, 1984

[54] ORAL COMPOSITION

[75] Inventors: Isao Iioka, Tokyo; Keiiti Yamagishi, Narashino; Hiroshi Sato, Tokyo; Nobuo Suganuma, Funabashi, all of Japan

[73] Assignee: Lion Corporation, Tokyo, Japan

[21] Appl. No.: 231,847

[22] Filed: Feb. 5, 1981

[30] Foreign Application Priority Data

Feb. 6, 1980 [JP] Japan ................... 55-13317

[51] Int. Cl.$^3$ .................. A61K 7/28; A61K 37/48
[52] U.S. Cl. ........................ 424/50; 424/58; 424/48; 424/94
[58] Field of Search ............... 424/50, 48, 94; 435/211

[56] References Cited

U.S. PATENT DOCUMENTS

| | | | |
|---|---|---|---|
| 3,574,824 | 4/1971 | Echeandia et al. | 424/50 |
| 3,622,661 | 11/1971 | King et al. | 424/50 |
| 3,686,393 | 8/1972 | Woodruff et al. | 424/50 |
| 3,720,762 | 3/1973 | Hatasa et al. | 426/651 X |
| 3,751,561 | 8/1973 | Wildi et al. | 424/48 |
| 3,981,989 | 9/1976 | Suganuma et al. | 424/50 |
| 3,991,177 | 11/1976 | Vidra et al. | 424/50 |
| 4,115,546 | 9/1978 | Vidra et al. | 424/50 |
| 4,140,758 | 2/1979 | Vidra et al. | 424/50 |
| 4,272,513 | 6/1981 | Gaffar | 424/58 |

FOREIGN PATENT DOCUMENTS

| | | |
|---|---|---|
| 503378 | 8/1973 | Japan . |
| 49-108252 | 11/1974 | Japan . |
| 53-26334 | 5/1978 | Japan . |
| 54-26339 | 2/1979 | Japan . |
| 54-31046 | 10/1979 | Japan . |
| 54-129138 | 10/1979 | Japan . |
| 55-19235 | 2/1980 | Japan . |
| 56-110609 | 8/1981 | Japan . |
| 56-110610 | 9/1981 | Japan . |
| 1427300 | 3/1976 | United Kingdom . |
| 2061727A | 5/1981 | United Kingdom . |
| 2073019A | 10/1981 | United Kingdom . |

OTHER PUBLICATIONS

Jacobs, Am. Perf. 61: 389 391 393, May 1953, How to Flavor Toothpaste.
Jocobs, Am. Perf. 61: 469–471, Jun. 1953, Flavoring Mouthwashes.
Merck Index, 9th Ed., (1976) Entrys 678 & 1867.

*Primary Examiner*—Shep K. Rose
*Attorney, Agent, or Firm*—Birch, Stewart, Kolasch & Birch

[57] ABSTRACT

A dextranase containing-oral composition is made more stable and has a good feeling to use by incorporating therein carvone and l-menthol together at a weight ratio of 1:9 to 8:2, preferably in a combined amount of 0.1 to 5% by weight of the composition. The composition may be a dentifrice composition.

15 Claims, No Drawings

4,469,673

ORAL COMPOSITION

BACKGROUND OF THE INVENTION

This invention relates to dextranase containing-oral compositions having a good feeling in use.

It is well known, for example, from U.S. Pat. No. 3,686,393 to incorporate dextranase in oral compositions as an active ingredient for caries prophylaxis to prevent the formation of dental plaque.

Unfortunately, dextranase tends to be deactivated by moisture, anionic surfactants and other ingredients in oral compositions. Several approaches have been proposed to stabilize dextranase as disclosed in U.S. Pat. Nos. 3,981,989, 3,991,177, 4,115,546 and 4,140,758 and G.B. Pat. No. 1,427,300.

Japanese Patent Publication No. 50-3378 discloses that a certain flavor is blended with dextranase to stabilize it, the flavor being selected from aliphatic alcohols having 7 to 17 carbon atoms and their esters, terpene hydrocarbones, phenol ethers and lactones.

When oral compositions are used in the mouth, they must have a good feeling in use. Merely blending a certain flavor as mentioned above is, however, insufficient to obtain oral compositions with a good feeling. It is therefore necessary to blend an additional flavor such as carvone, eugenol, methyl salicylate and cinnamic aldehyde to improve the feeling of compositions so as to meet the taste of consumers. However, carvone and similar flavors are believed to adversely affect the stability of dextranase as indicated in Japanese Patent Publication No. 50-3378. A problem still remains in stabilizing dextranase without impairing the feeling of oral compositions.

SUMMARY OF THE INVENTION

It is therefore an object of the present invention to provide an oral composition having a favorable feeling in use wherein dextranase is kept stable.

The present invention is based on the discovery that the above object can be attained by blending carvone and l-menthol into dextranase containing-oral compositions at a certain weight ratio. According to a first aspect of the present invention, carvone and l-menthol are blended at a weight ratio of from 1:9 to 8:2, preferably from 2:8 to 7:3, resulting in oral compositions with a good feeling in use wherein dextranase is kept stable. It has also been found that flavors such as eugenol, methyl salicylate and cinnamic aldehyde may be added to these oral compositions without reducing the stability of dextranase. The availability of such flavors as carvone, eugenol, methyl salicylate and cinnamic aldehyde in addition to conventional dextranase stabilizing-flavors will increase the variety of flavors which can be added to oral compositions.

The above and other objects, features and advantages of the present invention will become more apparent and understandable from the following descriptions.

DETAILED DESCRIPTION OF THE INVENTION

The oral composition of the present invention is contemplated to include toothpastes, toothpowders, liquid dentifrices, liquid oral refresher such as mouthwashes, solid oral refresher such as troches, and chewing gums. According to the present invention, carvone and l-menthol are blended in such an oral composition at a relative weight ratio of 1:9 to 8:2, more preferably 2:8 to 7:3.

The use of carvone and l-menthol at a weight ratio of 1:9 to 8:2 allows dextranase to be blended into the composition in a stable state, provides the composition with an optimum degree of refrigerant, body and pungency, and improves the feeling in use. The degrees of body and pungency are lacking and the feeling in use is abased at lower concentrations of carvone while dextranase becomes unstable and the composition becomes less refrigerant at higher concentrations of carvone. The objects of the present invention are attained only at a weight ratio of carvone to l-menthol within the above-specified range.

The stability of dextranase and the feeling of the composition are best when the combined amount of carvone and l-menthol is 0.1 to 5% by weight, more preferably 0.3 to 3% by weight based on the total weight of the composition. The degrees of body and refrigerant are low at combined amounts of less than 0.1% while the composition becomes too pungent at combined amounts of more than 5%. Further, excessive amounts of carvone and l-menthol will not contribute to an additional improvement in the stability of dextranase.

Carvone and l-menthol may be blended into an oral composition in an isolated or synthetic form while essential oils containing carvone or l-menthol may be used, for example, spearmint oil (containing carvone) and peppermint oil (containing l-menthol).

The present invention only requires to use carvone and l-menthol together and other conventional flavors may be additionally used, for example, aliphatic alcohols having 7 to 17 carbon atoms and their esters, terpene hydrocarbons, phenol ethers, and lactones. Further, those flavors which were believed to be detrimental to dextranase, for example, eugenol, methyl salicylate and cinnamic aldehyde may also be additionally blended in an amount of 0.001 to 0.5% by weight of the oral composition. This means that selection may be made from a wider variety of flavors so that an oral composition with an improved feeling to use may be easily prepared. It is contemplated that the oral composition may further include 0.1 to 0.5% by weight of anethole which serves to improve the quality of sweetness, thereby improving the taste of the composition.

The amount of dextranase blended is not particularly limited in this invention, but is generally 100–100,000 units per gram of the composition, preferably 1,000–50,000 units per gram of the composition. One unit of dextranase indicates the productivity of reducing sugars corresponding to 1 $\mu$g of glucose/min. when dextranase is incubated with a dextran substrate.

In addition to dextranase, the oral composition of this invention may further include other additional active ingredients, for example, enzymes such as amylase, protease, mutanase, lysozyme, lytic enzyme, etc., fluorine compounds such as alkali metal monofluorophosphates (e.g., disodium monofluorophosphate, dipotassium monofluorophosphate, etc.) and metal fluorides (e.g., sodium fluoride, stannous fluoride, etc.), stannous compounds, chlorhexidine salts, $\epsilon$-aminocaproic acid, tranexamic acid, aluminum chlorohydroxyallantoinate, dihydrocholesterol, glycyrrhetinates, glycerophosphate, sodium chloride, water-soluble inorganic phosphates, and the like alone or in admixture. Preferably alkali metal monofluorophosphates such as sodium monofluorophosphate may be combined with dextranase because they not only stabilize dextranase, but also retain sufficient dextranase in aged dentifrice compositions. Mutanase coacts with dextranase to provide a synergistic effect of dissolving dental plaque and preventing reformation of dental plaque. Dextranase may advantageously be combined with lytic enzyme to increase the efficacy thereof. Examples of the water-soluble inorganic phosphate are potassium and sodium salts of orthophosphoric acid, pyrophosphoric acid and polyphosphoric acid while the potassium salts are preferred.

The oral composition of this invention may further include other well-known ingredients depending on a particular type of the composition.

When the oral composition of the present invention forms a dentifrice composition, it may contain generally 20 to 90% by weight of an abrasive, particularly 20 to 60% by weight of an abrasive in the case of toothpastes. The abrasive may be selected from aluminum oxide compounds, dicalcium phosphate dihydrate and anhydride, silica, aluminosilicate, calcium carbonate, calcium pyrophosphate, aluminum silicate, insoluble sodium metaphosphate, magnesium tertiary phosphate, magnesium carbonate, calcium sulfate and synthetic resins and mixtures thereof.

The preferred main abrasive is an aluminum oxide compound as it ensures a further improvement in the stability of dextranase and the dentifrice itself. The aluminum oxide compounds include aluminum oxide (alumina, $Al_2O_3$) and hydrated aluminum oxides (hydrated aluminas, $Al_2O_3 \cdot nH_2O$ wherein $n > 0$, preferably $3 \geq n \geq 1$).

Many types of aluminas and hydrated aluminas are known including $\alpha$, $\gamma$, $\delta$, $\eta$, $\theta$, $\kappa$, $\chi$, $\rho$ and $\beta$ types classified in terms of crystal systems and physical properties. Among them, $\alpha$-alumina and hydrated $\alpha$-alumina are preferred because of high stability. The hydrated aluminas which can be used herein are gibbsite and bayerite (both represented by $Al_2O_3 \cdot 3H_2O$), boehmite and diaspore (both represented by $Al_2O_3 \cdot H_2O$) and the like. Among these aluminum oxide compounds, hydrated aluminas are preferred in view of abrasiveness, tooth abrasion and the like. Alumina trihydrates having the formula:

$$Al_2O_3 \cdot 3H_2O \text{ or } Al(OH)_3$$

are most preferred because of their mild abrasiveness. The preferred alumina trihydrate is gibbsite which is commercially available. The aluminum oxide compounds may be used alone or in admixture of two or more. In view of tooth cleaning and abrasing effects, the aluminum oxide compound should be in the form of particles having an average particle size of 1–50 microns, preferably 3–25 microns when measured by the sedimentation method.

In preparing dentifrice compositions, a binder may be blended generally in an amount of 0.3–5% by weight, including carrageenan, cellulose derivatives such as sodium carboxymethyl cellulose, alkali metal alginates such as sodium alginate, gums such as veegum and xanthan gum, synthetic binding agents such as polyvinyl alcohol, inorganic binding agents such as silica gel, aluminum silicate gel, etc. and mixtures thereof. Particularly, when an alkali metal monofluorophosphate is used as an additional active ingredient, carrageenan and alkali metal alginates may preferably be incorporated to improve the stability and feeling of dentifrices. Also, toothpastes containing kappa-carrageenan are stable and advantageous because kappa-carrageenan is more effective to smooth the toothpaste surface than usually available kappa-/iotacarrageenan mixtures.

A humectant may also be blended generally in an amount of 10–70% by weight, including sorbitol, glycerine, ethylene glycol, propylene glycol, 1,3-butylene glycol, polyethylene glycol, xylitol, maltitol, lactitol, etc. and mixtures thereof. Preferably 1–5% by weight of propylene glycol may be used as a binder disperser. Although larger amounts of propylene glycol used tend to reduce the retentivity of dextranase in an aged composition, a sorbitol-based humectant with an additive amount of propylene glycol is free of such tendency.

Also included are anionic surfactants such as water-soluble salts of the higher alkyl sulfates having 8 to 18 carbon atoms in the alkyl group (e.g., sodium lauryl sulfate and sodium mirystyl sulfate), water-soluble salts of sulfonated monoglycerides of higher fatty acids having 10 to 18 carbon atoms in the fatty acid group (e.g. sodium lauryl monoglyceride sulfonate and sodium coconut monoglyceride sulfonate), salts of amides of higher fatty acid having 12 to 16 carbon atoms in the fatty acid group with lower aliphatic amino acids (e.g. sodium-N-methyl-N-palmitoyl touride, sodium N-lauroyl sarcosinate and sodium N-lauroyl-$\beta$-alanine); nonionic surfactants such as alkyrol diethanol amides (e.g. lauroyl diethanol amide), stearyl monoglyceride, sucrose fatty acid esters having 12 to 18 carbon atoms in the fatty acid group (e.g. sucrose monolaurate and dilaurate), lactose fatty acid esters, lactitol fatty acid esters, maltitol fatty acid esters, condensates of sorbitan monostearate with approximately 60 moles of ethylene oxide, condensates of ethylene oxide with propylene oxide, condensates of propylene glycol and their derivatives (e.g. polyoxyethylene polyoxypropylene monolauryl ester), etc.; amphoteric surfactants such as those of betaine and amine acid types, etc., alone or in admixture in an amount of 0.5–7% by weight; a sweetener such as sodium saccharin, stevioside, neohesperidin dihydrocalcone, thaumatin, glycyrrhizin, perillartine, p-methoxycinnamic aldehyde, etc.; a preservative such as p-hydroxy methyl benzoic acid, p-hydroxy-butyl benzoic acid, etc.; gelatin, peptone and other ingredients. Toothpastes may be prepared by kneading the desired ingredients selected from the foregoing ingredients with a proper amount of water or other solvents.

The toothpaste composition according to this invention may generally have a pH of 4.5 to 10, preferably 6 to 8.5.

The thus prepared dentifrice composition may be ready for use only after it is packed in a suitable container, for example, aluminum tubes, laminate tubes having an aluminum foil laminated with a plastic lamina on either side, plastic tubes, bottles, aerosol containers or the like.

Other types of oral compositions may be prepared in accordance with conventional formulations and methods using a well-known base material.

The combined use of carvone and l-menthol at a weight ratio of 1:9 to 8:2 in a dextranase containing-oral composition according to the present invention not only allows dextranase to be kept stable or to fully exert its effect, but also increases the variety of flavors blendable into the composition so that the composition may be favorably accepted for oral application.

The following examples are illustrative of this invention and are not to be construed to limit the scope of the invention. All percents are by weight.

EXAMPLE 1

Toothpaste compositions (the present invention plus controls A and B) having the formulation shown in Table 1 were prepared. The quantity of dextranase in the compositions was measured both immediately after preparation and after aging for one month at 40° C., determining the retentivity of dextranase. In addition, an organoleptic test was carried out by a panel of specialized members to evaluate the feeling of these toothpaste compositions upon use. The results are shown in Table 1.

TABLE 1

| Ingredient | Invention (%) | Control A (%) | Control B (%) |
|---|---|---|---|
| Hydrated alumina (gibbsite $Al_2O_3.3H_2O$, average particle size 9 microns) | 50 | 50 | 50 |
| Sorbitol | 20 | 20 | 20 |
| Sodium lauryl sulfate | 1.5 | 1.5 | 1.5 |
| Lauroyl diethanol amide | 1.0 | 1.0 | 1.0 |
| Gelatin | 0.5 | 0.5 | 0.5 |
| Carrageenan | 0.5 | 0.5 | 0.5 |
| Sodium alginate | 0.5 | 0.5 | 0.5 |
| Sodium monofluorophosphate | 0.76 | 0.76 | 0.76 |
| Sodium saccharin | 0.1 | 0.1 | 0.1 |
| Carvone | 0.5 | 0.5 | — |
| l-menthol | 0.5 | — | 0.5 |
| Dextranase | 2000 U/g* | 2000 U/g | 2000 U/g |
| Water | Balance | Balance | Balance |
| Total | 100% | 100% | 100% |
| Analysis |  |  |  |
| Dextranase retentivity** | O | X | O |
| Feeling*** | O | X | V |

*U/g = units per gram of toothpaste
**Criterions for evaluating dextranase retentivity (aged at 40° C., 1 month)
O: retentivity higher than 70%
Δ: retentivity 30–70%
X: retentivity lower than 30%
***Criterions for evaluating feeling
O: sufficient in body and pungency, and refrigerant
X: less refrigerant
V: lack in body and pungency Then modifications were made to the dentifrice having the above formulation by changing the weight ratio of carvone to l-menthol while the combined amount of them was fixed to 1.0%. These modified compositions were similarly determined for dextranase retentivity and feeling. The results are shown in Table 2. Evaluation criterions are the same as in Table 1.

TABLE 2

| Carvone/l-menthol ratio | 0.5/9.5 | 1/9 | 2/8 | 5/5 | 7/3 | 8/2 | 9/1 |
|---|---|---|---|---|---|---|---|
| Dextranase retentivity | O | O | O | O | O | Δ | X |
| Feeling | V | O | O | O | O | O | X |

Table 2 reveals that dextranase is kept stable and the feeling of compositions is improved when carvone and l-menthol are blended together at a relative weight ratio of 1/9 to 8/2, particularly 2/8 to 7/3.

Additional dentifrice compositions having a formulation within the scope of the present invention and containing 0.2% by weight of methyl salicylate and cinnamic aldehyde, respectively, were prepared and determined for dextranase retentivity. The results of both the compositions were "O" according to the same evaluation criterion as above.

EXAMPLE 2

Toothpaste

| | |
|---|---|
| Hydrated alumina (gibbsite, average particle size 10 microns) | 50% |
| Propylene glycol | 2% |
| Sorbitol | 20% |
| Sodium lauryl sulfate | 1.5% |
| Lauroyl diethanol amide | 1.0% |
| Carrageenan | 1.0% |
| Sodium saccharin | 0.1% |
| l-menthol | 0.7% |
| Carvone | 0.3% |
| Dextranase | 2000 U/g |
| Water | Balance |
| | 100.0% |

EXAMPLE 3

Toothpaste

| | |
|---|---|
| Hydrated alumina (boehmite, average particle size 10 microns) | 40% |
| Silica | 3% |
| Sorbitol | 15% |
| Glycerin | 15% |
| Sodium lauryl sulfate | 1.0% |
| Lauroyl diethanol amide | 1.5% |
| Sodium alginate | 1.0% |
| Sodium monofluorophosphate | 0.76% |
| Gelatin | 0.3% |
| Sodium saccharin | 0.1% |
| l-menthol | 0.5% |
| Carvone | 0.3% |
| Anethole | 0.2% |
| Dextranase | 5000 U/g |
| Water | Balance |
| | 100.0% |

EXAMPLE 4

Toothpaste

| | |
|---|---|
| α-alumina (average particle size 5 microns) | 45% |
| Sorbitol | 25% |
| Sodium lauryl sulfate | 1.5% |
| Lauroyl diethanol amide | 0.5% |
| Carrageenan | 0.3% |
| Sodium alginate | 0.7% |
| Chlorhexidine hydrochloride | 0.01% |
| Sodium saccharin | 0.1% |
| l-menthol | 0.5% |
| Carvone | 0.5% |
| Anethole | 0.1% |
| Eugenol | 0.05% |
| Dextranase | 1000 U/g |
| Water | Balance |
| | 100.0% |

EXAMPLE 5

Toothpowder

| | |
|---|---|
| Dicalcium phosphate | 50% |
| Calcium carbonate | 20% |
| Glycerin | 10% |
| Sodium lauryl sulfate | 1.0% |
| Lactitol monolaurate | 1.0% |
| Gelatin | 0.3% |
| Sodium saccharin | 0.2% |
| l-menthol | 0.5% |

-continued

| | |
|---|---|
| Carvone | 0.9% |
| Peppermint oil | 0.4% |
| Dextranase | 10,000 U/g |
| Water | Balance |
| | 100.0% |

EXAMPLE 6

Toothpaste

| | |
|---|---|
| Calcium carbonate | 50% |
| Sorbitol | 20% |
| Lactitol monolaurate | 2.0% |
| Carrageenan | 1.0% |
| Sodium monofluorophosphate | 0.76% |
| Gelatin | 0.5% |
| Sodium saccharin | 0.1% |
| l-menthol | 0.3% |
| Carvone | 0.4% |
| Anethole | 0.05% |
| Spearmint oil | 0.5% |
| Dextranase | 3000 U/g |
| Water | Balance |
| | 100.0% |

EXAMPLE 7

Toothpaste

| | |
|---|---|
| Silica | 20% |
| Sorbitol | 40% |
| Glycerin | 20% |
| Sodium lauryl sulfate | 1.0% |
| Sodium alginate | 1.0% |
| Gelatin | 0.5% |
| Sodium saccharin | 0.2% |
| l-menthol | 0.3% |
| Carvone | 0.3% |
| Peppermint oil | 0.5% |
| Spearmint oil | 0.5% |
| Dextranase | 20,000 U/g |
| Water | Balance |
| | 100.0% |

EXAMPLE 8

Toothpaste

| | |
|---|---|
| Hydrated alumina (gibbsite, average particle size 10 microns) | 50% |
| Sorbitol | 30% |
| Sodium lauryl sulfate | 1.0% |
| Lauroyl diethanol amide | 1.2% |
| Carrageenan | 0.6% |
| Sodium alginate | 0.4% |
| Gelatin | 0.1% |
| Sodium saccharin | 0.1% |
| l-menthol | 0.7% |
| Carvone | 0.3% |
| Anethole | 0.3% |
| Eugenol | 0.1% |
| Linalool | 0.05% |
| Cineol | 0.05% |
| Dextranase | 2000 U/g |
| Water | Balance |
| | 100.0% |

EXAMPLE 9

Liquid dentifrice

| | |
|---|---|
| Glycerin | 35% |
| Sodium polyacrylate | 5% |
| Sodium lauryl sulfate | 1% |
| Sodium saccharin | 0.1% |
| Ethanol | 3% |
| l-menthol | 0.7% |
| Carvone | 0.3% |
| Dextranase | 5000 U/g |
| Water | Balance |
| | 100.0% |

EXAMPLE 10

Mouthwash

| | |
|---|---|
| Ethanol (90%) | 20% |
| Sodium saccharin | 0.3% |
| Polyoxyethylene (80 mol) sorbitan monolaurate | 0.5% |
| l-menthol | 1.5% |
| Carvone | 0.5% |
| Anethole | 0.4% |
| Eugenol | 0.2% |
| Linalool | 0.1% |
| Cineol | 0.1% |
| Dextranase | 30,000 U/ml |
| Water | Balance |
| | 100.0% |

EXAMPLE 11

Liquid oral refresher

| | |
|---|---|
| Ethanol | 30% |
| Glycerin | 15% |
| Sodium saccharin | 0.3% |
| Polyoxyethylene-hardened castor oil | 0.5% |
| l-menthol | 1.5% |
| Carvone | 0.5% |
| Anethole | 0.4% |
| Eugenole | 0.2% |
| Cineol | 0.1% |
| Orange oil | 0.2% |
| Dextranase | 3000 U/ml |
| Water | Balance |
| | 100.0% |

EXAMPLE 12

Troche

| | |
|---|---|
| Gum arabic | 6% |
| Glucose | 72% |
| l-menthol | 0.6% |
| Carvone | 0.4% |
| Spearmint oil | 0.2% |
| Dextranase | 3000 U/g |
| Water | Balance |
| | 100.0% |

EXAMPLE 13

Solid oral refresher

| | |
|---|---|
| Peppermint oil | 1 g |
| Lemon oil | 0.2 g |
| Eugenol | 0.1 g |
| Anethole | 0.2 g |
| Carvone | 0.3 g |
| Orris powder | 4 g |

-continued

| | |
|---|---|
| Xylite | 7 g |
| Licorice | 30 g |
| Cinnamon powder | 3 g |
| Ginger powder | 2 g |
| Clove powder | 1 g |
| Gum arabic solution | proper volume |
| Dextranase | 2000 U/g |

The solid ingredients were thoroughly comminuted, mixed together and then homogeneously blended with the liquid ingredients. The resulting mixture was granulated into free flowing granules.

EXAMPLE 14

Chewing gum

| | Parts by weight |
|---|---|
| Gum base | 20 |
| Calcium carbonate | 2 |
| Syrup | 15 |
| Powdered sugar | 60 |
| l-menthol | 0.5 |
| Carvone | 0.5 |
| Anethole | 0.1 |
| Dextranase | 2000 U/g |

The oral compositions of Examples 2 to 14 were found to give a good feeling on use and dextranase was retained stable in aged compositions.

What is claimed is:

1. An oral composition comprising:
dextranase in an amount of 100 to 100,000 units per gram of the composition; an anionic surfactant in an amount of 0.5 to 7% by weight of the composition; a flavor selected from the group consisting of eugenol, cinnamic aldehyde and mixtures thereof in an amount of 0.001 to 0.5% by weight of the composition; carvone; menthol; and water wherein carvone and l-menthol are present at a weight ratio of 2:8 to 7:3 and the combined amount of carvone and l-menthol is 0.3 to 3% by weight of the composition, whereby dextranase in the presence of water is stabilized.

2. An oral composition according to claim 1, wherein anethole is present in an amount of 0.01 to 5% by weight of the composition.

3. An oral composition according to claim 1, wherein cinnamic aldehyde is present.

4. An oral composition according to claim 1, in the form of a toothpaste, a liquid dentifrice, a mouthwash or a liquid oral refresher.

5. An oral composition according to claim 4, wherein at least one other oral composition ingredient is present and is selected from the group consisting of an abrasive, a humectant, a binder, a surface-active agent, a sweetner, another flavoring agent, another active ingredient and a solvent.

6. An oral composition according to claim 4, in the form of a toothpaste.

7. An oral composition according to claim 5, in the form of a liquid dentifrice.

8. An oral composition according to claim 5, in the form of a mouthwash.

9. An oral composition according to claim 6, wherein said at least one other oral composition ingredient includes an abrasive, a humectant, a binder, a sweetner and, a surface-active agent.

10. An oral composition according to claim 7, wherein said at least one other oral composition ingredient includes a humectant, a binder, a bactericide, a sweetner and, a surface-active agent.

11. An oral composition according to claim 8, wherein said mouthwash includes a sweetner and a surface-active agent.

12. An oral composition according to claim 4, wherein said composition has a pH of 4.5 to 10.

13. An oral composition according to claim 1, wherein said anionic surfactant is selected from the group consisting of water-soluble salts of the higher alkyl sulfates having 8 to 18 carbon atoms in the alkyl group, water-soluble salts of sulfonated monoglycerides of higher fatty acids having 10 to 18 carbon atoms in the fatty acid group, and salts of amides of higher fatty acid having 12 to 16 carbon atoms in the fatty acid group with lower aliphatic amino acids.

14. An oral composition according to claim 1, in the form of a toothpaste which includes an abrasive, a humectant, a nonionic surfactant, a binder, a sweetener, anethole and eugenol.

15. An oral composition according to claim 1, which includes anethole and eugenol.

* * * * *